United States Defensive Publication [19] (H) [11] T101,103

Sidhu et al. [43] Oct. 6, 1981

[54] ABSORBED HYDRAZIDE NUCLEATING AGENTS AND PHOTOGRAPHIC ELEMENTS CONTAINING SUCH AGENTS

[76] Inventors: Jasbir Sidhu, 29 Harley Rd., Harrow, Middlesex; Michael J. Simons; Miroslav V. Mijovic, both of Kodak Works, Wealdstone, Harrow, Middlesex, all of England

[21] Appl. No.: 238,185

[22] Filed: Feb. 26, 1981

Related U.S. Application Data

[62] Division of Ser. No. 60,549, Jul. 25, 1979, Pat. No. 4,278,748.

[51] Int. Cl.[3] ..... C07D 249/00

[52] U.S. Cl. ..... 430/598; 548/257

[57] ABSTRACT

Novel triazole-substituted phenylhydrazide nucleating agents are disclosed as well as silver halide photographic emulsions and elements containing silver halide grains capable of forming an internal latent image having the nucleating agents adsorbed to the surface of the silver halide grains.

5 Claims, No Sheets Drawing,

68 Pages Specification

The file of this unexamined application may be inspected and copies thereof may be purchased (849 O.G. 1221, Apr. 9, 1968).